US00PP36718P2

(12) United States Plant Patent
Li

(10) Patent No.: US PP36,718 P2
(45) Date of Patent: Jun. 3, 2025

(54) ***EUONYMUS* PLANT NAMED 'EcoFire'**

(50) Latin Name: *Euonymus alatus*
Varietal Denomination: EcoFire

(71) Applicant: UNIVERSITY OF CONNECTICUT, Farmington, CT (US)

(72) Inventor: Yi Li, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 18/887,070

(22) Filed: Sep. 17, 2024

(51) Int. Cl.
*A01H 5/00* (2018.01)
*A01H 6/00* (2018.01)

(52) U.S. Cl.
USPC ..... Plt./246
CPC ..... *A01H 6/00* (2018.05)

(58) Field of Classification Search
USPC ..... Plt./246
CPC ..... A01H 5/00; A01H 5/12
See application file for complete search history.

(56) References Cited

U.S. PATENT DOCUMENTS

PP36,198 P2 * 10/2024 Ranney ..... A01H 6/00
Plt./246

* cited by examiner

*Primary Examiner* — Kent L Bell

(74) *Attorney, Agent, or Firm* — Lisa Mueller; Casimir Jones SC

(57) ABSTRACT

A new and distinct *Euonymus* cultivar named 'EcoFire' which is characterized by a combination of its complete sterility and compact growth habit.

6 Drawing Sheets

GOVERNMENT FUNDING

This invention was made with government support under 2008-38914-19167, and 2010-38914-20996 awarded by the National Institute of Food and Agriculture. The government has certain rights in the invention.

Latin name of the genus and species: The Latin name of the genus and species of the novel variety disclosed herein is *Euonymus alatus.*

Variety denomination: The inventive cultivar of *Euonymus* disclosed herein has been given the variety denomination 'EcoFire'.

BACKGROUND OF THE INVENTION

Burning bush (*Euonymus alatus*) is known for its brilliant red fall color, rapid establishment, tolerance to environmental stress, and resistance to pests and diseases. Due to these traits, *Euonymus alatus* has been widely used in landscapes, with past annual sales reaching $8 million in Connecticut alone, and $60-70 million nationwide. However, its prolific seed production has led to its classification as invasive, resulting in bans or restrictions in several U.S. states, including New York, Massachusetts, New Hampshire, and Connecticut. Consequently, its market (e.g., sales) has significantly declined in the last decade.

In 2005, mature pollen grains of *Euonymus alatus* 'Compactus' (not patented) were treated with gamma radiation (3 kGy) and used to pollinate flowers of the same species. The resulting seeds were germinated, and seedlings were evaluated in the field for sterility. One line, named 'EcoFire', exhibited complete sterility, producing no seeds. While normal flowers developed, the young fruits dropped prematurely due to necrosis in the peduncle and fruit tissues.

Through a series of controlled pollination experiments between sterile 'EcoFire' and fertile *Euonymus alatus* lines, it was confirmed that 'EcoFire' is both male and female sterile.

Vegetative propagation of 'EcoFire' began in Connecticut in 2012, with field evaluations of seed production starting in 2016. Over this period (2016-2024), 35 'EcoFire' plants have consistently produced no seeds, unlike conventional *Euonymus alatus*, which can produce many thousands of seeds per plant under the same conditions. Additional 'EcoFire' plants propagated in 2016 have also remained seedless. The original 18-year-old plant has not produced any seeds as of 2024. Therefore, over three generations, 'EcoFire' plants have consistently demonstrated complete sterility.

'EcoFire' is a spreading, dwarf variety with an upright, flat-topped growth habit, reaching about 5.5 to about 6.5 feet in height and width after about 11 years. 'EcoFire' shares morphological similarities with *Euonymus alatus* 'Compactus', (not patented) but is more compact, about 80 to about 90% of the size of *Euonymus alatus* lines, such as, 'Compactus' (not patented). Specifically, the color and shape of the stems, foliage, and floral organs of 'EcoFire' are visually indistinguishable from the stems, foliage, and floral organs of 'Compactus'.

Asexual Reproduction: Asexual reproduction of 'Ecofire', by way of cuttings, was first performed in June 2012 in Storrs, CT. Through two (2) subsequent generations, the unique features of this cultivar have proven to be stable and true to type. The Royal Horticultural Society (R.H.S.) Colour Chart used to provide the colors described herein was published in 2007 (Fifth Edition).

SUMMARY OF THE INVENTION

The cultivar 'Ecofire' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Ecofire'. These characteristics in combination distinguish 'Ecofire' as a new and distinct *Euonymus alatus* cultivar:

1. *Euonymus alatus* 'Ecofire' is a spreading, dwarf variety with an upright, flat-topped growth habit that reaches about 5.5 to about 6.5 feet in height and width after about 11 years. It is about 80-90% of the size of *Euonymus alatus* 'Compactus'; and
2. *Euonymus alatus* 'Ecofire' is completely sterile. Its fruits drop prematurely due to its sterility.

BOTANICAL DESCRIPTION OF THE PLANT

Figure 1:
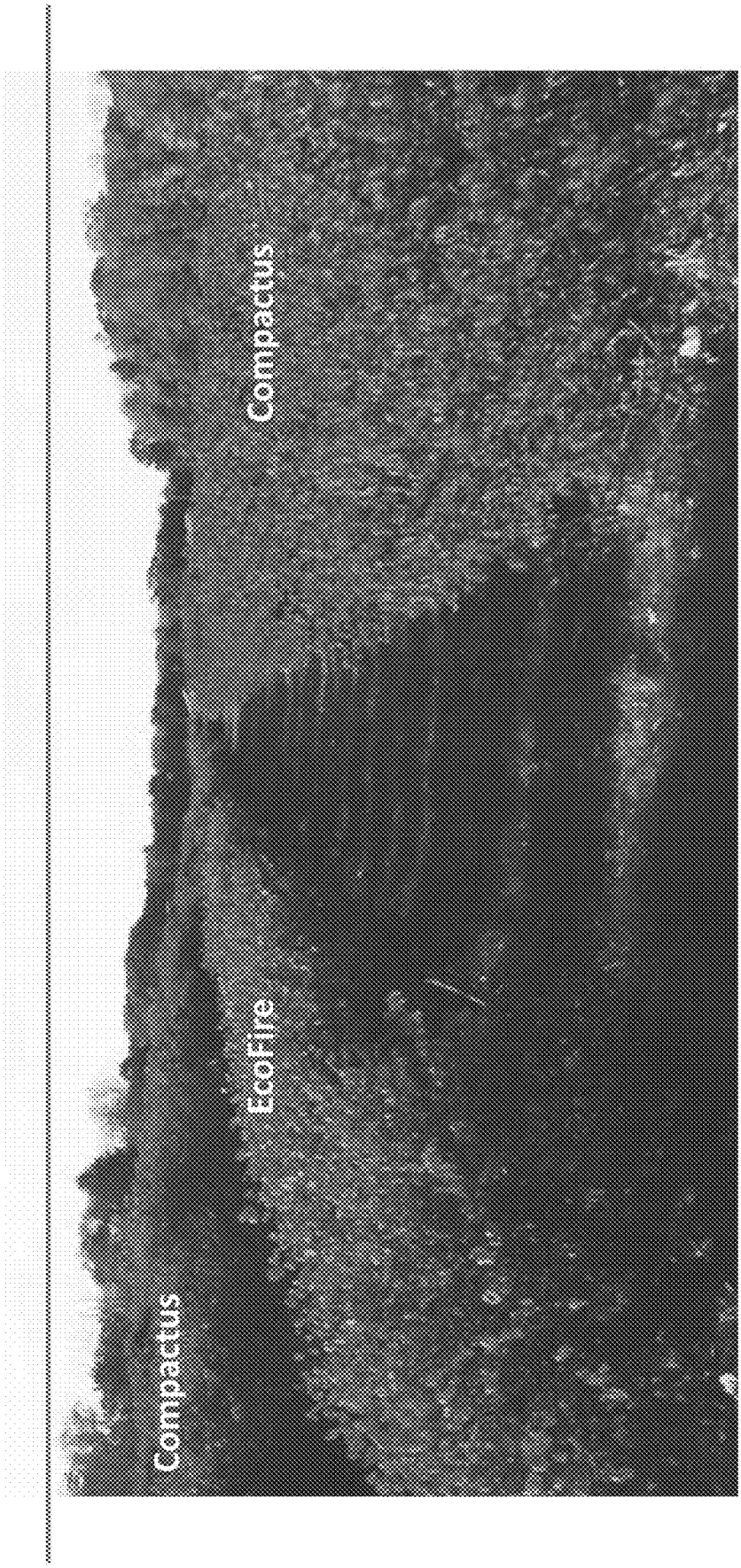
FIG. 1 shows a comparison of the fall foliage color in twelve-year-old plants of *Euonymus alatus* 'EcoFire' and twelve-year-old plants of *Euonymus alatus* 'Compactus' (not patented). As shown in this figure, sterile *Euonymus alatus* 'EcoFire' plants display the same vibrant fall foliage color as *Euonymus alatus* 'Compactus'.
Figure 2:
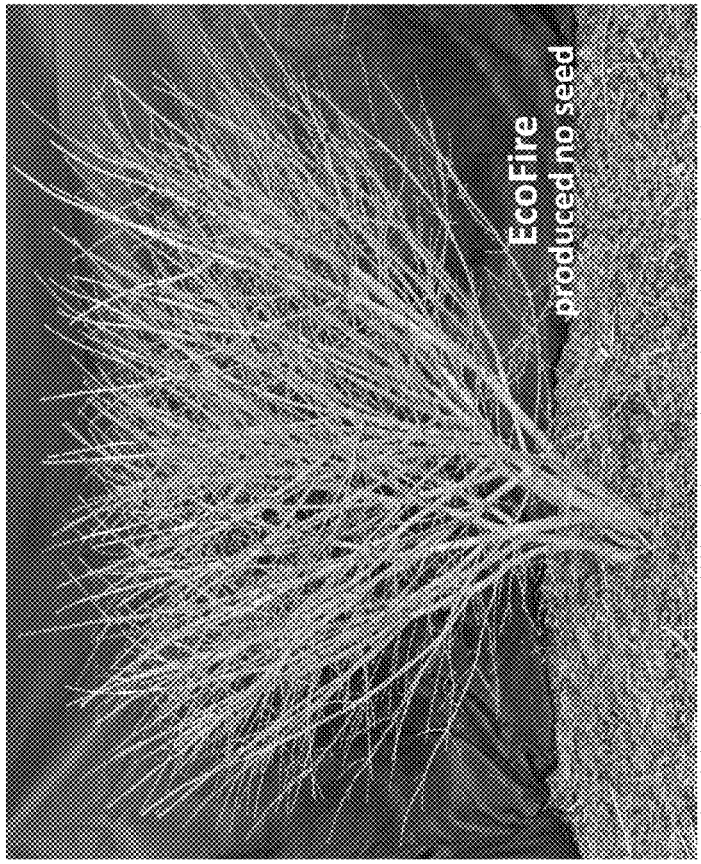
FIG. 2 shows a comparison of the seed production from nine-year-old plants of *Euonymus alatus* 'EcoFire' and nine-year-old plants of *Euonymus alatus* 'Compactus'. *Euonymus alatus* 'EcoFire' plants produce no fruits or seeds, whereas *Euonymus alatus* 'Compactus' produces more than 10,000 fruits/seeds per plant.
Figure 2:
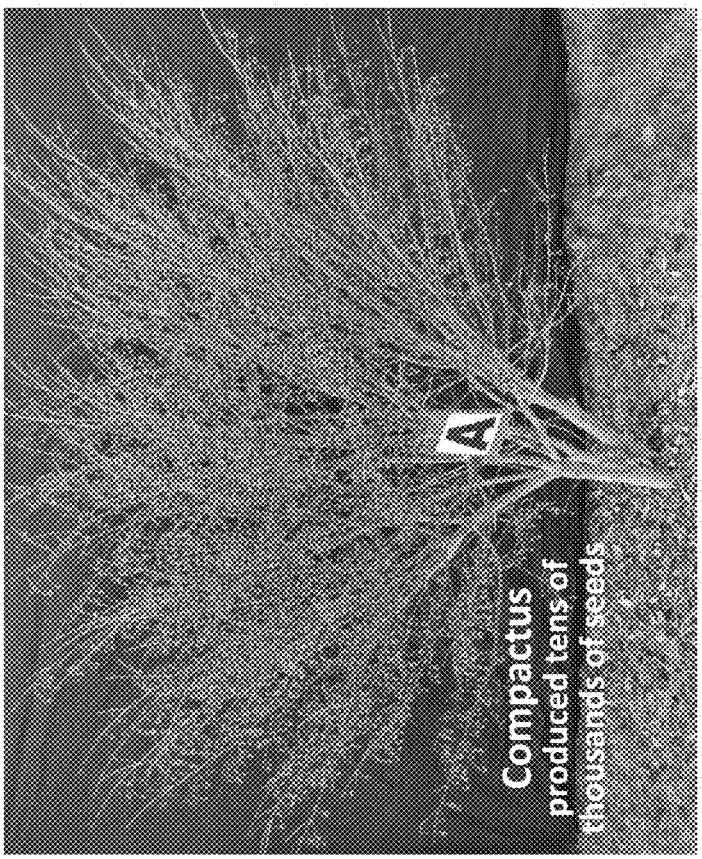
Figure 3:
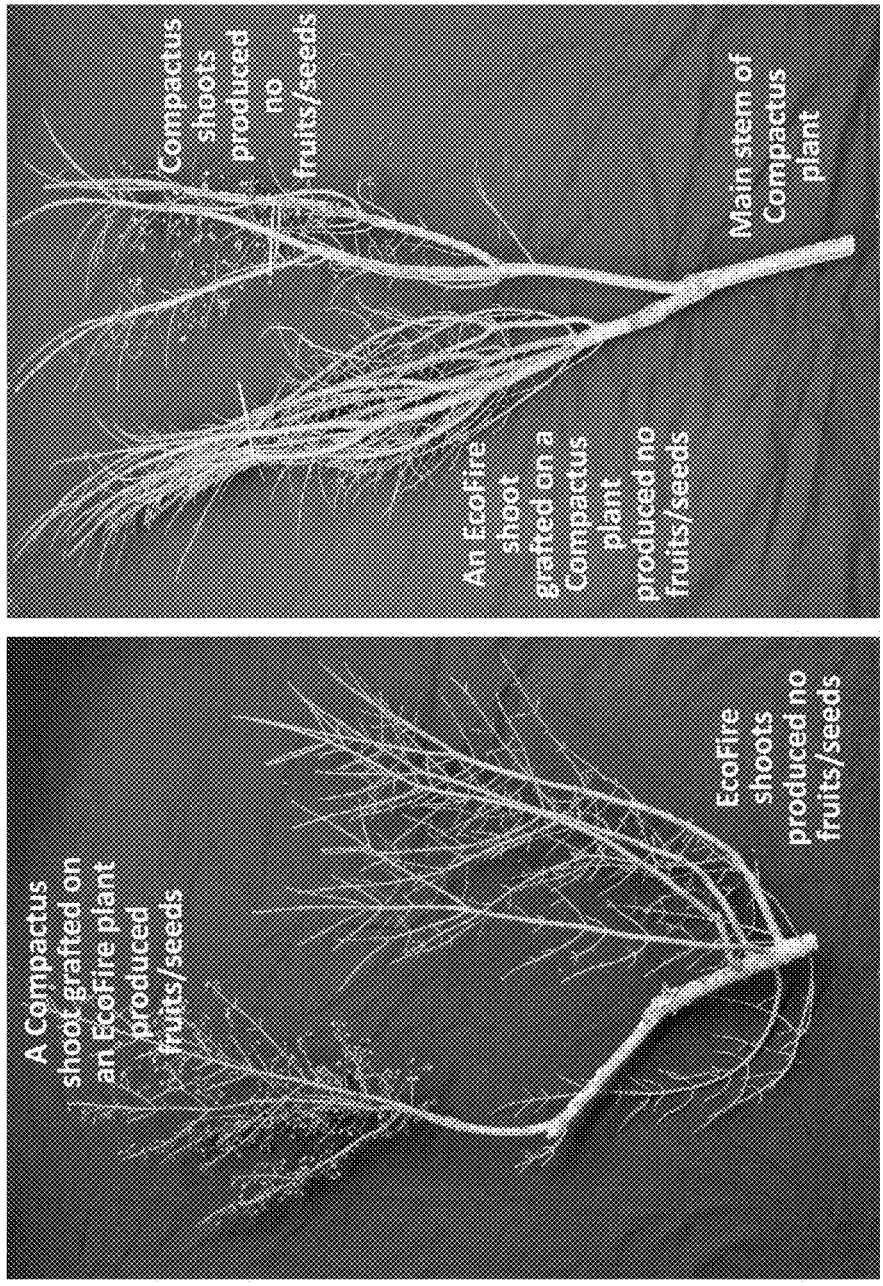
FIG. 3 shows grafts of *Euonymus alatus* 'Compactus' on *Euonymus alatus* 'EcoFire' (left) and *Euonymus alatus* 'EcoFire' grafted on to *Euonymus alatus* 'Compactus' (right). Seed product occurred in *Euonymus alatus* 'Compactus' grafted onto *Euonymus alatus* 'EcoFire', whereas *Euonymus alatus* 'EcoFire' grafted onto *Euonymus alatus* 'Compactus' produced no seeds.
Figure 4:
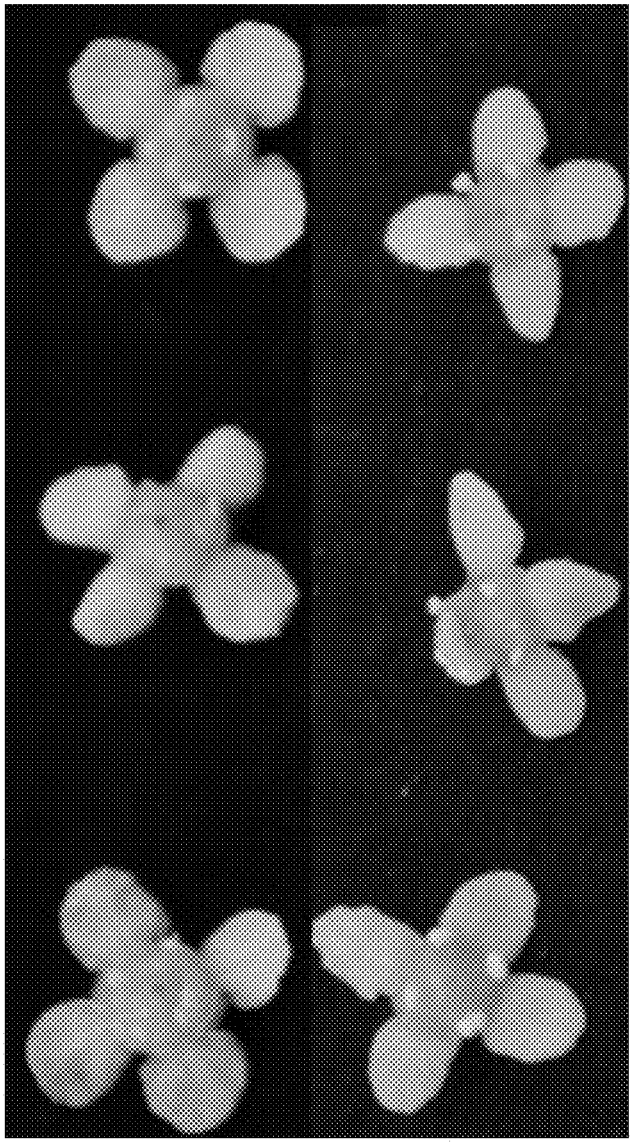
FIG. 4 shows a comparison of the mature flowers of *Euonymus alatus* 'Compactus' (top three) and *Euonymus alatus* 'EcoFire' (bottom three).
Figure 5:
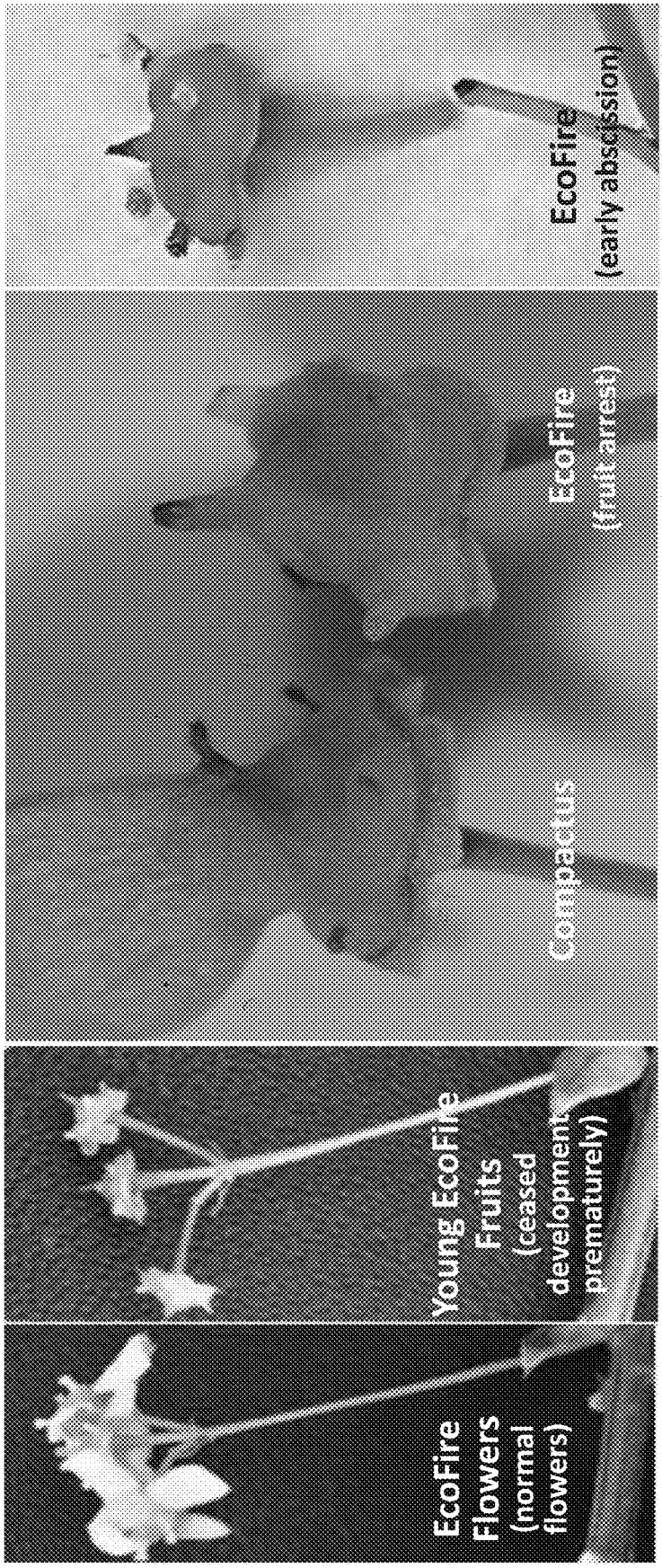
FIG. 5 shows premature cessation of fruit development in *Euonymus alatus* 'EcoFire'. Young fruits of *Euonymus alatus* 'EcoFire' cease development within two weeks after flowering and drop prematurely due to necrosis in the peduncle tissues.
Figure 6:
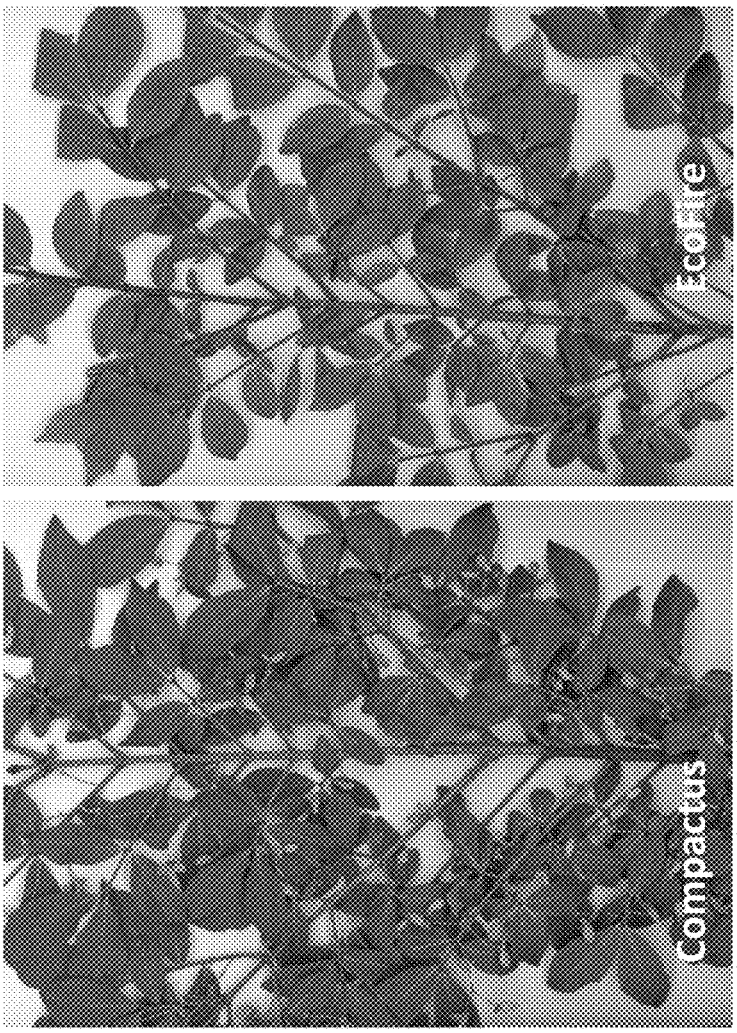
FIG. 6 shows a comparison between the shoot and leaf morphology of *Euonymus altus* 'EcoFire' and *Euonymus altus* 'Compactus'. No significant differences are observed between *Euonymus alatus* 'EcoFire' and 'Compactus'.

The following observations and measurements made in August of 2024 describe averages from a sample set of 35 specimens of 16-year-old 'EcoFire' plants on a Research Farm in Storrs, CT.

Those skilled in the art will appreciate that certain characteristics will vary with older or, conversely, with younger plants. 'EcoFire' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions.

Growth habit: Compact, upright, and vase shaped.

Average height (from base to top of foliage): Eleven-year-old plants of *Euonymus alatus* 'Ecofire' grown in Storrs, CT are 6 feet (72 inches).

Average width: Eleven-year-old plants of *Euonymus alatus* 'Ecofire' grown in Storrs, CT are 6 feet (72 inches).

Growth rate: 5-6 inches per year.

Vigor: Moderate, with growth about 80 to about 90% of *Euonymus alatus* 'Compactus' variety.

Propagation: Stem cuttings are taken from first-year shoots in late June to early July, about 3.5 to 4.5 inches long with 4 to 6 nodes. A rooting powder containing auxin is applied to the basal ends of the cuttings, which root in 4-6 weeks. The cuttings are grown in greenhouse pots, then moved to an overwintering greenhouse where temperatures range from about 38° F. to about 53° F. during the winter months in Connecticut. This method is similar to conventional burning bush propagation.

Time to produce marketable plants: About 2 to about 6 years, depending on the desired plant size.

Disease and pest resistance: Similar to conventional burning bush, with no noted susceptibility to diseases or pests.

Environmental tolerances: Hardy in USDA Zones 4-8, tolerating temperatures from about −30° F. to about 100° F. Tolerant of wind, rain, drought, and various soil types.

Stems, foliage, and floral organs: The color and shape is visually indistinguishable from *Euonymus alatus* 'Compactus'.

Seed and fruit production: None, due to male and female sterility. Table 1 below shows a comparison of the seed production in 'EcoFire' and 'Compactus'. Specifically, Table 1 shows that 'Compactus' produces thousands of seeds, but 'EcoFire' produces no seeds.

TABLE 1

| | Year | | | | |
|---|---|---|---|---|---|
| Plant Type | 2016 | 2017 | 2018 | 2019 | 2020 |
| Compactus-1[1] | 1,039 | 4,125 | 7,987 | 9,870 | 13,083 |
| Compactus-2[1] | 1,135 | 4,237 | 8,427 | 10,803 | 14,045 |
| Copmactus-3[1] | 1,227 | 4,655 | 8,267 | 10,358 | 13,673 |
| 35 vegetatively propagated EcoFire plants[1] | 0 | 0 | 0 | 0 | 0 |

| | Year | | | |
|---|---|---|---|---|
| Plant Type | 2021 | 2022 | 2023 | 2024 |
| Compactus-1[1] | 13,516 | 14,480 | NC[2] | NC |
| Compactus-2[1] | 14,222 | 15,193 | NC | NC |
| Copmactus-3[1] | 13,860 | 15,023 | NC | NC |
| 35 vegetatively propagated EcoFire plants[1] | 0 | 0 | 0 | 0 |

[1]Vegetatively propagated in 2012.

[2]NC: Seeds produced in 2023 and 2024 from three 'Compactus' plants were more than previous years but not counted.

*Euonymus alatus* 'EcoFire' and 'Compactus' share several characteristics. Both cultivars exhibit similar leaf and flower morphology, featuring medium to dark green leaves that turn bright red in the fall and small, inconspicuous yellow-green flowers. Both *Euonymus alatus* 'EcoFire' and 'Compactus' exhibit similar root morphology, including comparable numbers and lengths of roots. Their overall growth habits are also comparable, as both are deciduous shrubs with a dense, rounded form. Over 11 years, 'Compactus' typically reaches 6.6 feet in height, while 'EcoFire' grows to about 6.0 feet under full sunlight in deep, well-fertilized soil. Both plants adapt well to varying soil conditions and thrive in full sun to partial shade under three experimental conditions: (1) full sunlight with deep, well-fertilized soil, (2) partial shade with deep, well-fertilized soil, and (3) partial shade with marginal soil. Despite these similarities, notable differences distinguish the two. 'EcoFire' is completely sterile (male and female sterile) and does not produce seeds, whereas 'Compactus' is known for prolific seed production. Additionally, 'EcoFire' exhibits a slightly slower growth rate, reaching approximately 90% of the height of 'Compactus'. Its internode length is also slightly reduced, measuring about 95% of that in 'Compactus'. Furthermore, 'EcoFire' experiences premature flower and young fruit drop due to browning and necrosis of the pedicels, a trait not observed in 'Compactus'. While 'Compactus' begins fruit and seed production in its third year, 'EcoFire' remains fruitless and seedless.

TABLE 2

| | 'Compactus' as Male Parent | 'EcoFire' as Male Parent |
|---|---|---|
| 'Compactus' as Female Parent | Seeds produced | No seed produced |
| 'EcoFire' as Female Parent | No seed produced | No seed produced |

COMPARISONS WITH THE PARENT PLANT

*Euonymus alatus* 'EcoFire' differs from *Euonymus alatus* 'Compactus' in its complete sterility and compact growth habit. While *Euonymus alatus* 'Compactus' produces seeds prolifically, 'EcoFire' remains seedless. Additionally, 'EcoFire' grows at a slower rate and is more compact, reaching about 6 feet in height and width over about 11 years. The color and shape of the flowers of 'EcoFire' are similar (virtually indistinguishable) to those of 'Compactus', but the fruits drop prematurely due to sterility. Specifically, the stamens, pistil, and overall flower exhibit a yellowish-green hue, approximately RHS 115A.

Under both greenhouse and field conditions, one to two-year-old *Euonymus alatus* 'EcoFire' and 'Compactus' exhibit similar root morphology. This includes comparable root density, number, branching patterns, thickness, and lengths. Additionally, the newly formed young root tissues of both cultivars display a healthy white coloration, approximately RHS NN155C.

*Euonymus alatus* 'EcoFire' and 'Compactus' exhibit no significant differences in their shoots' current and prior year's growth, except for a slight reduction in 'EcoFire'. Specifically, 'EcoFire' shows approximately a 5% decrease in internode length and about a 10% reduction in overall height in 11-year-old plants compared to 'Compactus'. Both cultivars demonstrate comparable shoot diameters, with consistent texture, morphology, and coloration. The color of the shoots aligns with recognized standards, as referenced in The 2007 Royal Horticultural Society (R.H.S.) Colour Chart. Specifically, the new or current-year shoots are typically a light to medium green, similar to or slightly lighter than RHS NN137A.

*Euonymus alatus* 'EcoFire' and 'Compactus' exhibit no significant differences in their shoot branching characteristics, including angles, patterns, or morphology. The coloration of the branches in both 'EcoFire' and 'Compactus' aligns with recognized standards, as referenced in The 2007 Royal Horticultural Society (R.H.S.) Colour Chart. Specifically, the branches are generally a medium to dark brown, approximately RHS 85B.

*Euonymus alatus* 'EcoFire' and 'Compactus' exhibit no significant differences in their leaf characteristics. Both cultivars possess simple, opposite leaves that are elliptic to obovate in shape, measuring approximately 1 to 3 inches (2.5 to 7.5 cm) in length and 0.5 to 1 inch (1.3 to 2.5 cm) in width. The leaf apex is acute, the base is cuneate to attenuate, and the margins are finely serrated (crenulate to serrulate). The texture of the leaves is chartaceous to herbaceous, with a smooth, glabrous surface on both sides. Venation is pinnate, featuring a prominent central vein with secondary veins branching off at intervals. During the growing season, the leaves display a medium to dark green color, transitioning to a vibrant bright red in the fall. These colorations align with The 2007 Royal Horticultural Society (R.H.S.) Colour Chart, with the summer foliage corresponding to RHS NN137A (medium green) and the autumn foliage to RHS 45A (scarlet red).

*Euonymus alatus* 'EcoFire' and 'Compactus' exhibit no significant differences in their petiole characteristics. Both cultivars feature petioles that are approximately ¼ inch (6 mm) in length and slender in diameter. The texture of the petioles is smooth and glabrous, with a coloration that corresponds to a medium green, closely matching the summer foliage, approximately RHS NN137A.

*Euonymus alatus* 'EcoFire' and 'Compactus' exhibit no significant differences in their flowering seasons. Both cultivars typically bloom from late spring to early summer, specifically from May to June. This flowering period has been consistently observed in three locations of Connecticut where these plants are cultivated.

*Euonymus alatus* 'EcoFire' and 'Compactus' exhibit no significant differences in their inflorescence characteristics. Both cultivars produce small, inconspicuous, yellow-green flowers (RHS 115A) arranged in axillary cymes, typically comprising three flowers per cluster.

*Euonymus alatus* 'EcoFire' and 'Compactus' exhibit no significant differences in their bud characteristics. Both cultivars feature conical buds that are approximately ⅛ inch (3 mm) in length and about 1/16 inch (1.5 mm) in diameter. The buds are smooth in texture and display a mix of colors, include medium green (RHS NN137A), scarlet red (RHS 45A), and brown (RHS 85B).

*Euonymus alatus* 'EcoFire' and 'Compactus' exhibit no significant differences in their flower characteristics. Both cultivars produce small, inconspicuous, four-petaled flowers that are approximately 6 mm in diameter. The flowers are yellow-green (RHS 115A) in color and typically bloom in late spring to early summer.

*Euonymus alatus* 'EcoFire' and 'Compactus' exhibit no significant differences in their petal and sepal characteristics. Both cultivars produce small, four-petaled flowers with petals approximately 6 mm in length and 3 mm in width, featuring a rounded shape, smooth texture on both surfaces, and a pale yellow-green color (RHS 145A). The sepals are about 1.5 mm in both length and width, also rounded with a smooth texture, and display a green hue.

*Euonymus alatus* 'EcoFire' and 'Compactus' exhibit no significant differences in their peduncle and pedicel characteristics. Both cultivars produce small, yellow-green (RHS 115A) flowers borne on slender, smooth peduncles and pedicels. The peduncles (flower stalks) are approximately ¼ inch (6 mm) in length, while the pedicels (individual flower stems) measure about ⅛ inch (3 mm) in length. Both structures (the peduncle and pedicel) have a smooth texture and display a medium green color (RHS NN137A).

*Euonymus alatus* 'EcoFire' and 'Compactus' exhibit no significant differences in their floral organ characteristics. Both cultivars possess perfect flowers, each containing both male and female reproductive structures. Each flower typically comprises four stamens with small, rounded anthers approximately 1 mm in length, displaying a yellowish-green color consistent with the overall hue of the flower. Pollen production is moderate, with pale yellow (RHS 11D) pollen grains. The singular pistil measures about 1.5 mm in length and features a short style of approximately 0.5 mm, matching the flower's yellow-green color (RHS 115A). The stigma is capitate (rounded) and shares the same yellowish-green hue as the rest of the floral components. However, 'EcoFire' is both male and female sterile; it does not produce viable pollen and fails to set fruit or seeds. This sterility is attributed to the premature drop of mature flowers and young fruits due to browning and necrosis of the pedicels. In contrast, 'Compactus' is fertile and capable of producing viable seeds.

What is claimed is:

1. A new and distinct cultivar of *Euonymus* plant named 'EcoFire', substantially as described and illustrated herein.

* * * * *